United States Patent [19]

Kaplan et al.

[11] Patent Number: 5,385,901
[45] Date of Patent: Jan. 31, 1995

[54] METHOD OF TREATING ABNORMAL CONCENTRATIONS OF TNF α

[75] Inventors: Gilla Kaplan, New York, N.Y.; Elisabeth P. Sampaio, Rio de Janeiro, Brazil

[73] Assignee: The Rockefeller University, New York, N.Y.

[21] Appl. No.: 955,936

[22] Filed: Oct. 2, 1992

Related U.S. Application Data

[60] Division of Ser. No. 834,588, Feb. 12, 1992, abandoned, which is a continuation of Ser. No. 655,087, Feb. 14, 1991, abandoned.

[51] Int. Cl.[6] .................. A61K 31/535; A61K 31/44; A61K 31/445
[52] U.S. Cl. ........................... 514/231.5; 514/231.2; 514/282; 514/327; 514/331; 514/348
[58] Field of Search ............ 514/327, 348, 282, 231.2, 514/231.5, 331

[56] References Cited

U.S. PATENT DOCUMENTS 2,830,991 4/1958 Keller et al. ................... 260/281

FOREIGN PATENT DOCUMENTS 1185273 3/1970 United Kingdom .
WO92/09203 6/1992 WIPO .

OTHER PUBLICATIONS

Eger et al., "Synthesis, Central Nervous System Activity and Teratogenicity of a Homothalidomide", Arnzeim.-Forsch./Drug Research, 40 (II), No. 10, pp. 1073–1075 (1990).
Eriksson et al., "Synthesis and alkaline hydrolysis of some n-substituted phthalimides", Acta Pharm. Suecica, 10, pp. 63–74 (1973).
Fabro et al., "Teratogenic Activity Of Thalidomide And related Compounds", Life Sciences, vol. 3, pp. 987–992, Pergamon Press, Inc. (1964).
Fickentscher et al., "Stereochemical Properties and Teratogenic Activity of Some Tetrahydrophthali-
(List continued on next page.)

Primary Examiner—Raymond J. Henley, III
Assistant Examiner—T. J. Criares
Attorney, Agent, or Firm—Mathews, Woodbridge & Collins

[57] ABSTRACT

Compounds of the structure

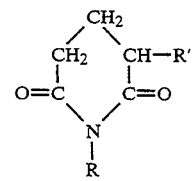

wherein R is selected from the group consisting of hydrogen, alkyl radicals of 1–6 carbon atoms, the phenyl radical, and the benzyl radical; and wherein R' is selected from the group consisting of the phthalimido radical and the succinimido radical and of the structure

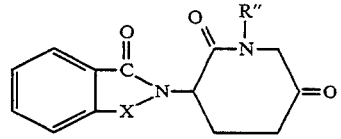

II wherein X is $CH_2$ or C=O; R" is H, $-CH_2CH_3$, $-C_6H_5$, $-CH_2C_6H_5$, $-CH_2CH=CH_2$, or

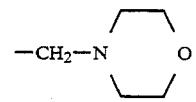

and hydrolysis products of said compounds wherein R" is H and the piperidino ring or both the piperidino and the imido ring are hydrolyzed are useful for the control of abnormal concentrations of TNF α manifested in septic shock, cachexia and HIV infection without substantially effecting the concentration of other cytokines.

18 Claims, 7 Drawing Sheets

OTHER PUBLICATIONS mides", *Molecular Pharmacology*, 13, pp. 133–141, Academic Press, Inc. (1977).

Flohé et al. "Studies on the Hypothetical Relationship of Thalidomide–induced Embryopathy and Collagen Biosynthesis", *Arnzeim.-Forsch./Drug Research*, 31 (I), No. 2, pp. 315–320 (1981).

Hendler, "The Oxygen Breakthrough", pp. 217–219, William Morrow and Company, New York (1989).

Hendler et al., "Thalidomide For Autoimmune Disease", *Medical Hypotheses*, 10, pp. 437–443 (1983).

Jönsson et al., "Chemical structure and teratogenic properties: I. Synthesis and teratogenic activity in rabbits of some derivatives of phthalimide, isoindoline-1-one, 1,2-benzisothiazoline-3-one-1,1-dioxide and 4(3H)-quinazolinone", *Acta Pharm. Suecica*, 9, pp. 431–446 (1972).

Jönsson, "Chemical structure and teratogenic properties: III. A review of available data on structure-activity relationships and mechanism of action of thalidomide analogues", *Acta Pharm. Suecica*, 9, pp. 521–542 (1972).

Jönsson, "Chemical structure and teratogenic properties: IV. An outline of a chemical hypothesis for the teratogenic action of thalidomide", *Acta. Pharm. Suecica*, 9, pp. 543–562 (1972).

Koch, "4 Thalidomide and Congeners as Anti–inflammatory Agents", *Progress in Medical Chemistry*, vol. 22, pp. 166–242, Elsevier Science Publishers, B.V. (Biomedical Division) (1985).

Matsuyama et al., "Cytokines and HIV infection: is AIDS a tumor necrosis factor disease?", *AIDS 1991*, vol. 5, No. 12, pp. 1405–1417 (1991).

Smith et al., "Studies on the Relationship Between the Chemical Structure and Embryotoxic Activity of Thalidomide and Related Compounds", *Chemical Structure and Embryopathy*, pp. 194–209 (1964).

METHOD OF TREATING ABNORMAL CONCENTRATIONS OF TNF α

This invention was made with Government support under AI 22616-05 AI 07012-25 awarded by the Allergy and Infections Institute. The Government has certain rights in the invention.

RELATED APPLICATIONS

This is a continuation of Ser. No. 07/834,588 filed Feb. 12, 1992, now abandoned, which in turn is a continuation of Ser. No. 07/655,087 filed Feb. 14, 1991, now abandoned.

BACKGROUND OF THE INVENTION

Debilitation, i.e. loss of weight, strength, vascular weakness, and other symptoms are natural sequelae of many diseases which afflict humans. These may include, for example bacterial infections such as tuberculosis; viral infections, particularly retroviral infections including HIV infections such as AIDS; various forms of arthritis particularly rheumatoid and degenerative; ulcerative colitis; regional enteritis; and the like. Human patients with these symptoms may present with an acute condition such as septic shock or with a chronic condition such as cachexia.

U.S. Pat. No. 2,830,991 describes a class of therapeutic agents of the general formula I

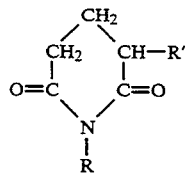

wherein R is selected from the group consisting of hydrogen, alkyl radicals containing 1-6 carbon atoms, the phenyl radical, and the benzyl radical; and wherein R' is selected from the group consisting of the phthalimido radical and the succinimido radical.

The subject matter of this patent and of any other patents or publications identified in this disclosure are incorporated herein by reference.

Preferred compounds within the scope of the above formula I, for use in this invention are:
3-phthalimido-2,6-dioxo-1-ethyl piperidine
3-phthalimido-2,6-dioxo-1-phenyl piperidine
3-phthalimido-2,6-dioxo-1-benzyl piperidine
3-phthalimido-2,6-dioxo-1-allyl piperidine
3-phthalimido-2,6-dioxo-piperidine As described in the patent, the compounds are produced by reacting an aliphatic dicarboxylic acid, which contains five carbon atoms in a straight chain, the methylene groups of which are substituted by the substituents in accordance with the appropriate general formula, with urea or substitution products thereof or with a primary amine or an acid amide in such manner that water is split off and the ring is closed. If an amino group is present in the aliphatic chain, this group must not exist in free form in this stage of the process, since otherwise there is the danger of this amino group participating in an undesirable manner in the reaction. Instead of using the dicarboxylic acid, it is also possible to employ functional derivatives thereof, such as acid halides, acid esters and acid amides.

Compounds of the glutaminic acid series may be used as starting materials for the present invention. In this case also, the acid halides, esters and amides of glutaminic acid may be employed instead of the acid itself. It is known that glutaminic acids tends to form 5-membered rings with a free amino group. This reaction is undesirable for the purposes of the present invention. The amino group must therefore be substituted or protected prior to the ring-closing reaction. The protection of the amino group may be carried out, when using products of the glutaminic acid series, by introducing the phthalyl, succinyl or like radical in a manner known per se. The proportions of the components used for the ring formation must be such that at least 1 mol of the compound yielding the imide nitrogen is used to one mol of the glutaminic acid component.

The first compound listed above is prepared by reacting 27.7 g. of N-phthalyl glutaminic acid with 66 g. of a 33% solution of ethyl amine in water and slowly heating in an oil bath 160°-180° C., the mixture being maintained at this temperature for 15 to 20 minutes. The reaction product is recrystallised from alcohol by fractionation. It melts at 209° C.

The last compound listed above prepared by reacting 13 g. of phthalyl glutaminic acid anhydride and 6 g. of urea in 75 cc. of absolute xylene for 4 hours at the boiling point of the mixture. Formation of a sublimate takes place with evolution of ammonia and carbon dioxide. The xylene is then distilled off in vacuo and the residue recrystallized from 95% alcohol by fractionation. In addition to some phthalimide and phthalyl glutamine, the required $N_2$-phthalyl glutaminic acid imide is obtained, having a melting point of 269°-271° C.

In the patent, the compounds are disclosed as having low toxicity and as useful for certain spasmolytic and antihistaminic effects. The compound 3-phthalimido-2,6-dioxopiperidine is disclosed as being particularly useful as a sedative. This compound was marketed as a sedative under the generic name thalidomide. It was subsequently discovered to be teratogenic and was withdrawn from the market.

Despite its teratogenicity, thalidomide has long been employed for the treatment of erythema nodosum leprosum (ENL) an accute inflammatory state occurring in lepromatous leprosy. See, for example Mellin, G. W., and M. Katzenstein. *N. Engl. J. Med.* 267:1184 (1962). More recently, it has been shown to be useful in the treatment of graft-versus-host disease by Vogelsany, G. B., S. Taylor, G. Gordon and A. D. Hess. *Transplant Proc.* 23:904 (1986); for treatment of reheumatoid arthritis by O. Gutierrez-Rodriguez, P. Starusta-Bacai and O. Gutierrez-Montes. *The Journal of Rheumatology* 16:2 158 (1989); and for treatment of aphthous ulceration in patients positive for HIV antibody. *Brit. Med. J.* 298:432 (1989).

The tumor necrosis factor (TNF-α) is one of several cytokines released mainly by mononuclear phagocytes together with several other cytokines in response to stimuli to the immune system. It is required for a cell mediated immune response to overcome infections. As its name suggests, it is associated with the destruction of tumor cells. It is not present in measureable amounts in normal sera, but appears, often very rapidly, in response to immunostimulators such as bacterial and viral infections, particularly HIV infections. In the case of chronic infection it may be found in the sera at relatively high or low levels for extended periods of time. It may also appear suddenly in high concentrations in response to release of a toxin by an invading bacteria. It is markedly elevated in ENL.

TNF-α has been recognized as manifesting a dose dependent toxicity. If present at low levels for too long a period it results in cachexia. At high levels even for a short time it results in septic shock.

Cachexia is a general weight loss and wasting occurring in the course of a chronic disease. More specifically, it is a weight loss not accounted for by decreased caloric intake. It is associated with cancer, the opportunistic infections of AIDS, inflammatory diseases, parasitic diseases, tuberculosis, high dose IL-2 therapy and the like. It is a chronic condition related to chronic diseases.

Septic shock is an acute condition usually, but not always attributed to infection or to toxic substances in the tissue. It is characterized by hypotension due to loss of vascular tone. It may result in patient collapse, or even death if not treated promptly and efficiently.

The retroviruses are a broad group of RNA viruses which, during their replication, employ the reverse transcription enzyme (RT) to convert a RNA message to DNA. The retroviridae family of viruses includes lentiviruses (visna, maedi, progressive pneumonia virus -"slow viruses"), spumaviruses (foamy viruses) and oncornaviruses (types A, B, C, D, RNA tumor viruses). The retroviruses have been shown to infect murine, avian, feline, primate, and human species.

The human immunodeficiency virus (HIV-1) or human T-Cell lymphotropic viruse (HTLV-III) which causes Acquired Immune Deficiency Syndrome (AIDS), AIDS related complex (ARC) and other AIDS related diseases is a retrovirus. TNF-α functions in an autocrine manner in the induction of HIV-1 expression (G. Poli et al, PNAs Vol 87 p 782, 1990).

It is apparent, therefore, that it is necessary to control the concentration of TNF-α in the sera to avoid the debilitating effects of abnormal concentrations of this cytokine including, for example, cachexia and septic shock.

Other cytokines which are necessary for a proper immune response are also produced by mononuclear phagocytes. These include, for example, various interleukins such as IL-1, IL-6, IL-8 and the granulocyte macrophage colony stimulating factor, GM-CSF. Still other cytokines are produced by the T-cells. It is desirable to control the concentration of TNF without appreciably affecting the concentration and activity of other cytokines.

Heretofore, antiinflammatory and immunosuppresive steroids such as prednisolone and dexamethasone have been employed to treat the debilitating effects of TNF-α. Unfortunately, these therapeutic agents also block the production of other cytokines so that the patients become susceptible to life threatening infections.

BRIEF SUMMARY OF THE INVENTION

It has now been discovered that the debilitating effects of toxic concentrations of TNF-α, whether acute or chronic, can be controlled in humans by treating a human patient in need of such treatment with an anti-debilitating amount of a compound within the scope of the above description. Typically the treatment may be either oral or parenteral, for example intravenously or subcutaneously.

It has further been discovered that certain compounds within the scope of the above formula as well as other closely related compounds are especially useful for the practice of this invention. These compounds are presently preferred for the therapeutic purposes of the inventions. These preferred compounds include those represented by formula II

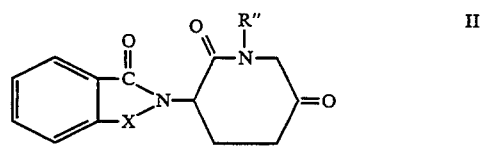

wherein X is $CH_2$ or $C=O$; R is H, $-CH_2CH_3$, $-C_6H_5$, $-CH_2C_6H_5$, $-CH_2CH=CH_2$, or

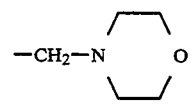

and hydrolysis products of said compounds wherein R is H and the peperidino ring or both the peperidino and the imido ring are hydrolyzed.

Especially preferred compounds within the ambit of the above definition are represented by the formulas:

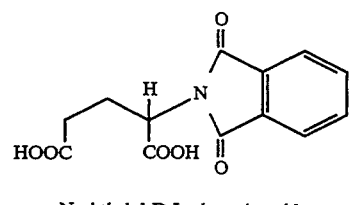

N-phthalyl-D,L-glutamic acid
A

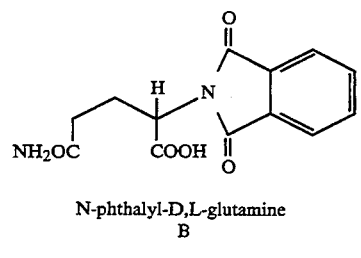

N-phthalyl-D,L-glutamine
B

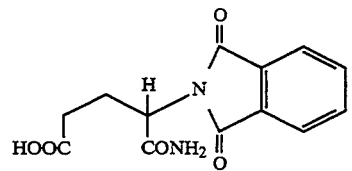

N-phthalyl-D,L-isoglutamine
C

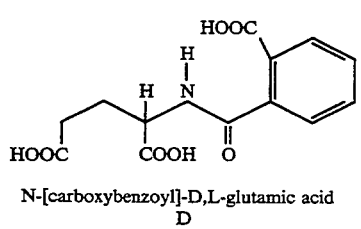

N-[carboxybenzoyl]-D,L-glutamic acid
D

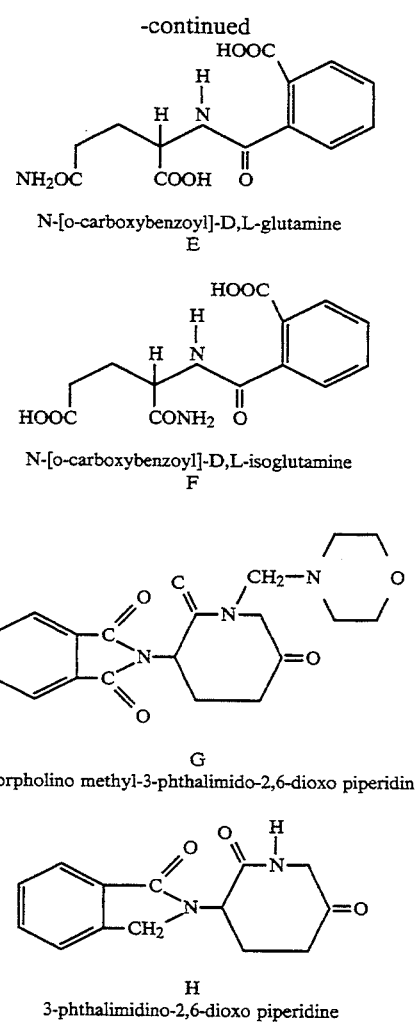

N-[o-carboxybenzoyl]-D,L-glutamine
E

N-[o-carboxybenzoyl]-D,L-isoglutamine
F

G
1-Morpholino methyl-3-phthalimido-2,6-dioxo piperidine

H
3-phthalimidino-2,6-dioxo piperidine

Most of the non-hydrolyzed compounds whose formulas are given above can be prepared by the processes described in the aforesaid U.S. Pat. No. 2,830,991. The preparation of the phthalimidine compounds is described in U.S. Pat. No. 3,705,162. U.S. Pat. No. 3,563,986 describes the preparation of the morpholino substituted compounds. The hydrolytic compounds are prepared by standard hydrolysis procedures several of which will be known to the skilled artisan.

The compounds used in the invention can exist as racemic mixtures. The racemic mixtures and separate isomers are included within the scope of the invention.

The compounds may be administered alone, but will normally be employed in a composition containing a pharmaceutically acceptable carrier. It may be advantageous, as will be discussed more fully below to administer the selected compound or compounds together with an effective amount of a therapeutic agent appropriate for treating the cause of the abnormal concentration of TNF-$\alpha$, for example with an antibacterial agent if the condition under treatment is shock caused by the sudden release of large amounts of a toxin because of bacterial infection.

THE DRAWINGS

FIGS. 1a, 1b, 1c; 2, 3, show the effects of thalidomide on TNF-$\alpha$ production in the presence of various reagents.

FIGS. 4 through 7 show the results of studies conducted to establish the utility of the compounds of this invention to inhibit HIV-1 RT activity.

The drawings and the balance of this disclosure will be better understood by recognizing the meanings of certain abbreviations. CWP-ML means cell wall protein of *Mycobacterium leprae*. ENL means erythema nodosum leprosum. GM-CSF means granulocyte macrophage colony-stimulating factor. PPD means purified protein derivative of tuberculin. PBMC means peripheral blood mononuclear cells.

The studies described hereinafter will be recognized by those skilled in the art as establishing that the compounds of this invention selectively inhibit the production of human TNF-$\alpha$ without substantially affecting the production of other proteins or of total serum protein. Therefore, although the compounds of the invention will not cure diseases, they will significantly improve the quality of life of the patients. An important consequence of the study is the finding that TNF-$\alpha$ secretion is not totally inhibited. This is important since, as indicated above, TNF-$\alpha$ appears to be an essential mediator in the immune response.

There follows a complete description of one procedure for establishing the ability of the compounds of this invention to inhibit the production of TNF-$\alpha$ without inhibiting the production of other cytokines.

Monocyte Isolation.

PBMC obtained by Ficoll-Hypaque (Pharmacia Fine Chemicals, Piscataway, N.J.) density centrifugation were rosetted with neuraminidase-treated (Vibrio cholerae neuraminidase; Calbiochem-Behring Corp. La Jolla, Calif.) sheep erythrocytes (Scott Laboratories, Friskville, R.I.) (SRBC rosetting), and the nonrosetted cells were counted (E$^-$ population monocytes enriched). $10^6$ cells were cultured at 37° C. in 24-well plates (Corning Glass Works, Corning, N.Y.) in 1 ml of RPMI 1640 (Gibco Laboratories, Grand Island, N.Y.) supplemented with 10% AB$^+$ serum, 100 U/ml penicillin, 100 $\mu$g/ml streptomycin, and 2 mM 1-glutamine. Adherent E$^-$ cells were used for the studies.

Cytokine Agonist

LPS of *Salmonella minnesota* R595 (List Biological Laboratories, Campbell, Calif.) was diluted in PBS, pH 7.4, and used at 1 g/ml; Purified protein derivative of tuberculin (PPD) was purchased from Statens Seruminstitut, Copenhagen, Denmark; CWP-ML was prepared using known and published methods. The concentrations of the stimulating agents were those known to induce optimal TNF-$\alpha$ protein production by cultured monocytes. The endotoxin content of solutions and mycobacterial preparations was estimated by the Limulus amebocyte lysate assay (LAL; Whittaker M. A. Bioproducts, Walkersville, Md.). All solutions used contained less than 10 pg/ml of endotoxin.

Cytokine Induction

Adherent E$^-$ cells were stimulated with 1 $\mu$g/ml of LPS, 10 $\mu$g/ml of PPD, or 10 $\mu$g/ml of CWP-ML for up to 18-20 h. At various times, supernatants were harvested, centrifuged to remove cells and debris, and kept frozen until use ($-20°$ C.).

TNF-$\alpha$ Assay

TNF-$\alpha$ concentration in the supernatants was determined with a TNF-$\alpha$ specific ELISA, specific for the biologically active molecule. Assays were performed in 96-well plates (Nunc Immunoplates, Roskilde, Denmark) coated with the affinity-purified rabbit anti-TNF-$\alpha$ antibody (0.5 $\mu$g/ml; 12–16 h; 4° C.) and blocked for 2 h at room temperature with PBS/0.05% Tween 20 (Sigma Chemical Co., St. Louis, Mo.) containing 5 mg/ml BSA. After washing, 100 $\mu$l of TNF-$\alpha$ standards, samples, and controls were applied to the wells, and the plates were incubated for 12–24 h at 4° C. After the incubation, plates were washed and a second antibody, horseradish peroxidase (HRP)-conjugated mouse monoclonal anti-TNF-$\alpha$, diluted 1:2,000 in PBS/BSA/Tween, was applied to the wells and incubated for 2 h at room temperature. The color reaction was developed with the OPD substrate (0.4 mg/ml o-phenylenediamine [Sigma Chemical Co.] in 24 mM citric acid, 51 mM sodium phosphate, pH 5.0 [phosphate-citrate buffer: Sigma Chemical Co.] containing 0.012% hydrogen peroxide [$H_2O_2$; Fisher Scientific Co., Pittsburgh, Pa.]) and absorbance read at 492 nm in an automated ELISA reader (Dynatech Laboratories, Inc., Alexandria, Va.).

IL-1 Assays

IL-1 levels were determined using a commercial ELISA kit (Cistron Biotechnology, Pine Brook, N.J.) according to the manufacturer's specifications. IL-1 levels are expressed as pico-grams per milliliter of protein.

IL-6 Assay

IL-6 levels were determined using a biological assay as described by Finkelman et al. Proc. Natl. Acad. Sci. USA. 83:9675 (1986). Proliferation of 7TD1 hybridoma cell line specifically sensitive to IL-6 was measured by colorimetric determination of hexosaminidase levels, Laudegren et al J. Immunol. Methods. 67:379 (1984), and values for IL-6 in the samples were obtained by interpolation from a standard curve. 1 U/ml of IL-6 corresponds to the concentration that yields half-maximal growth.

Granulocyte/Macrophage CSF GM-CSF Assay

GM-CSF levels were determined using a commercial ELISA kit (Genzyme, Boston, Mass.) according to the manufacturer's specifications, and were expressed as picograms per milliliter of protein.

Thalidomide Inhibition

The thalidomide used in this study was the purified drug (racemic mixture: D[+] and L [−] forms) (lot No. JB-I-114; Andrulis Research Corporation, Beltsville, Md.). The compound was shown to be at least 99% pure, as analyzed by Fourier Transform Infrared Spectrum. It was then diluted in DMSO (Sigma Chemical Co.); further dilutions were done in sterile PBS.

Percentage inhibition of TNF-$\alpha$ secretion was calculated as: 100×[1-(TNF-$\alpha$ experimental/TNF-$\alpha$ control)]; where TNF-$\alpha$ experimental represents TNF-secretion by stimulated monocytes that were cultured in the presence of thalidomide, and TNF-$\alpha$ control represents TNF-$\alpha$ secretion by stimulated monocytes that were cultured in the absence of the drug. Monocytes cultured in medium containing equivalent amounts of DMSO in the presence or absence of the stimulating agent were used as controls for thalidomide-treated cells. Neither thalidomide nor DMSO had any effect on cell viability or function at the concentrations used.

Protein Synthesis

Human monocytes were cultured in Teflon beakers in methionine-free RPMI with 10% AB+ serum at 37° C. for 1 h, when 200 $\mu$Ci/ml $^{35}$S-methionine (1,153 $\mu$Ci/mmol; ICN Biomedicals Inc., Calif.) was added to the cultures for the next 3 h with or without the stimulating and the suppressive agent. At the end of the labeling period, $^{35}$S-labeled cells were washed twice in ice-cold PBS and lysed directly in 500 $\mu$l lysis solution (10 mM Tris-HCl buffer, pH 7.4 150 NaCl, 1 mM EDTA, and 1% SDS). Resolving 8% SDS-PAGE was performed overnight. The gel was washed, dried, and analyzed by autoradiography at −70° C. using XAR-5 radiographic film (Kodak, Rochester, N.Y.) with an intensifying screen.

RESULTS OF THIS STUDY

Monocytes were enriched from PBMC of normal donors and stimulated in vitro for 18–20 h with bacterial LPS and mycobacterial products, known agonist of monocyte TNF-$\alpha$ synthesis and secretion. Thalidomide suppressed LPS-stimulated TNF-$\alpha$ production (FIG. 1A) with a 50% inhibitory concentration (IC$_{50}$) of 1–4 $\mu$g/ml, and 90% inhibition observed at 10 $\mu$g/ml (18–20-h assay). Similar results were obtained when PPD and CWP-ML were used as stimulants (FIG. 1, B and C, respectively).

FIG. 1 shows the effect of thalidomide on (A) bacterial endotoxin (LPS, 1 $\mu$g/ml), (B) PPD, (10 $\mu$g/ml), and (C) CWP-ML (10 $\mu$g/ml)- induced TNF-$\alpha$ production. Monocytes were stimultaneously incubated with 2 ng/ml to 10 $\mu$g/ml of thalidomide in the culture medium. Control cells were cultrued in medium alone. A dose-dependent inhibition of TNF-$\alpha$ secretion by thalidomide is apparent. No detectable production of TNF-$\alpha$ protein was observed in supernatants of unstimulated monocytes. Data represent mean ± SD of 15(A), two (B), and one (C) different experiments, respectively.

The inhibition of TNF-$\alpha$ secretion by thalidomide was dependent upon the state of monocyte stimulation as shown in Table 1. Preincubation of unstimulated monocytes with thalidomide, followed by removal of the drug before LPS stimulation, did not lead to suppression. By comparison, when LPS and thalidomide were added stimultaneously to the cultures, irreversible suppression occurred, even when the drug was removed after a few hours (Table 1). Therefore, the thalidomide sensitive reaction(s) occurs only after the LPS induction of TNF-$\alpha$ production.

TABLE 1

|   | h | | | h | | | |
|---|---|---|---|---|---|---|---|
| A | 0–4 | 0 | 0 | 4–20 | 0 | + | 100 |
| B | 0–4 | + | 0 | 4–20 | 0 | + | 90 ± 4.6 |
| C | None | 0 | 0 | 0–4 | + | + | 48 ± 15 |
| D | 0–4 | + | + | 4–20 | 0 | + | 56 ± 0.5 |
| E | None | 0 | 0 | 0–20 | + | + | 52 ± 9.3 |

Human monocytes cultured in 24-well plates were preincubated with the inhibitory drug with or without the stimulating agent. After 4 h, the cultures were washed, medium was replaced, and LPS was added again for the next 16 h. Culture supernatants were recovered at the different periods and TNF-$\alpha$ levels determined as described. LPS-inducted release of TNF-$\alpha$ by monocytes cultured for 20 h in the absence of thalidomide (A). No inhibitory action of thalidomide was detected when the drug was washed away before the addition of the stimulating agent (B). Thalidomide-induced inhibition of TNF- production in the present of LPS after 4 h of stimulation (C), which persisted even after the drug was washed away (D). Control experiment in which thalidomide was kept in the cultures with the stimulating agent during the whole assay (E). Data represent mean ± SD of two different experiments.

The inhibition of LPS-stimulated TNF-$\alpha$ secretion by thalidomide occurs in a setting in which many other proteins are being synthesized by both constitutive and induced mechanisms. Thus, a simple explanation for the effect of the drug on TNF-$\alpha$ production could be a suppression of overall protein synthesis.

FIG. 2 illustrates the effect of thalidomide on the pattern and quantity of proteins synthesized after a 3-h pulse of $^{35}$S-methionine. The total incorporation of isotope into TCA-precipitable proteins as well as the intensity of most of the individual bands on SDS-PAGE of LPS-triggered monocytes remained unchanged after thalidomide treatment.

In FIG. 2 can be seen the effect of thalidomide on protein synthesis by human peripheral blood monocytes. Electrophoretic analysis of lysates from monocytes incubated with $^{35}$S-methionine was performed. Cells were stimulated in vitro with and without LPS in the presence or absence of thalidomide at 1 and 4 $\mu$g/ml. TCA-precipitable radioactivity (10% TCA precipitation) was measured by liquid scintillation counting. The amount of radioactivity in the pellets expressed as $cpm \times 10^{-3}$ and represents the mean of three precipitates with a SD of 10%. Neither total radioactivity nor the pattern of most of the protein bands in the gel was affected by thalidomide (lane 1) unstimulated cells, $3.3 \times 10^{-2}$ cpm in TCA precipitates; (lane 2) cells stimulated with 1 $\mu$g/ml LPS, $4.2 \times 10^{-2}$ cpm in TCA precipitate; (lane 3) cells stimulated with LPS in the presence of 1 $\mu$g/ml thalidomide, $4.2 \times 10^{-2}$ cmp in TCA precipitate; (lane 4) cells stimulated with LPS in the presence of $\mu$g/ml thalidomide, $4.1 \times 10^{-2}$ cpm in TCA precipitate; (lanes 5 and 6) cells incubated only with thalidomide at 1 or 4 $\mu$g/ml, respectively, $3.2 \times 10^{-2}$ and $2.8 \times 10^{-2}$ cpm in TCA precipitates, respectively.

Several cytokines are produced by monocytes in response to LPS in addition to TNF-$\alpha$, including IL-1 and IL-6. FIG. 3 shows that thalidomide exerts a selective effect by suppressing only TNF-$\alpha$ secretion LPS-stimulated monocytes. Whereas 4 $\mu$g/ml thalidomide suppressed TNF-$\alpha$ production (41.9% inhibition) (FIG. 3A), neither IL-1 (FIG. 3B), IL-6 (FIG. 3 C), nor GM-CSF production (FIG. 3 D) was influenced by the drug. Similar but more extensive selective suppression was observed with much higher (up to 20 $\mu$g/ml) concentrations of thalidomide. It was also observed that the D (+) enantiomer appeared to be more active than the L(−) enantiomer.

FIG. 3 shows the levels of different cytokines tested in culture supernatants of human monocytes stimulated with LPS for 6 h (A-C) or 20 h (D) in the presence or absence of 4 or 10 $\mu$g/ml of thalidomide. Data represent mean ± SD of six different experiments for TNF-$\alpha$ and IL-1 determinations and three experiments for IL-6 and GM-CSF measurements. About 41.9±14.6% and 52.8±14.7% inhibition of TNF-$\alpha$ secretion was found in the presence of 4 and 10 $\mu$g/ml of thalidomide, respectively. "Cont" illustrates unstimulated cells cultured in medium. No effect on IL-1, IL-6, or GM-CSF secretion was detected in these cultures.

The following study establishes the utility of compounds of the invention for reducing TNF-$\alpha$ concentration in HIV infections. TNF-$\alpha$ is known to induce HIV replication. Similarly, it is known that peripheral blood monocytes from HIV infected patients secrete higher amounts of TNF-$\alpha$ than do monocytes from uninfected individuals. TNF-$\alpha$ is a cytokine capable of inducing viral expression in cells chronically infected with HIV. The art, therefore, has long been concerned with discovering products capable of inhibiting TNF-$\alpha$ production in HIV infected patients. The compounds of this invention are capable of so doing. This fact was established in studies using the known and commercially available chronically infected cell lines U1 and ACH-2, a promonocytic cell line and a T-lymphocytic cell line. The procedure employed is described by Poli et al. (1990) Proc. Nat'l. Acad. sci. U.S.A. Vol. 87, pp 782-785.

Briefly, the expression of HIV was upregulated by the addition of $10^{-7}$ m of phorbol 12-myristate 13-acetate (PMA) or 1 $\mu$g/ml of TNF$_\alpha$ to ACH-2 and U1 cells. The cells were suspended at $4 \times 10^5$ per ml in RMP1 1640 medium (M.A. Bioproducts) supplemented with 10% (vol/vol) fetal calf serum in the presence of the selected amount of stimulator at 37° C. in 5% $CO_2$/95% air for 48 hours, the supernatants collected and tested for the presence of $Mg^{++}$ dependent reverse transcriptase activity using the procedure of Willy et al (1988) J. Virol. 62, 139-147.

For the test, 10 $\mu$l of supernatants were added to 50 $\mu$l of a mixture containing 5 $\mu$g per ml of poly(rA) p(dT) 12-18, (Pharmacia), 5 mM $MgCl_2$ and 10 $\mu ci/\mu l$ of $^{32}$P-labeled deoxythymidine 5'- triphosphate (dTTP-Amersham), and the mixture was incubated for 1½ hours at 37° C. Eight microliters of the mixture were spotted onto DE81 paper (Whatman), air-dried and washed 5 times in 2×standard saline citrate buffer, and two additional times with 95% ethanol. The paper was dried, cut and radioactivity assayed. The results are shown in the figures.

FIG. 4 shows the results of tests in which 5, 10 and 50 $\mu$g/ml of thalidomide (THAL) and the known TNF$_\alpha$ inhibitor pentoxyfylline (PTN) were used to inhibit reverse transcriptase production with the cell line U1. For the comparison, reverse transcriptase activity in the absence of the inhibitor was taken as 100%. It will be seen that at a concentration of 50 $\mu$g/ml, thalidomide was as effective as PTN.

Figure 1A:
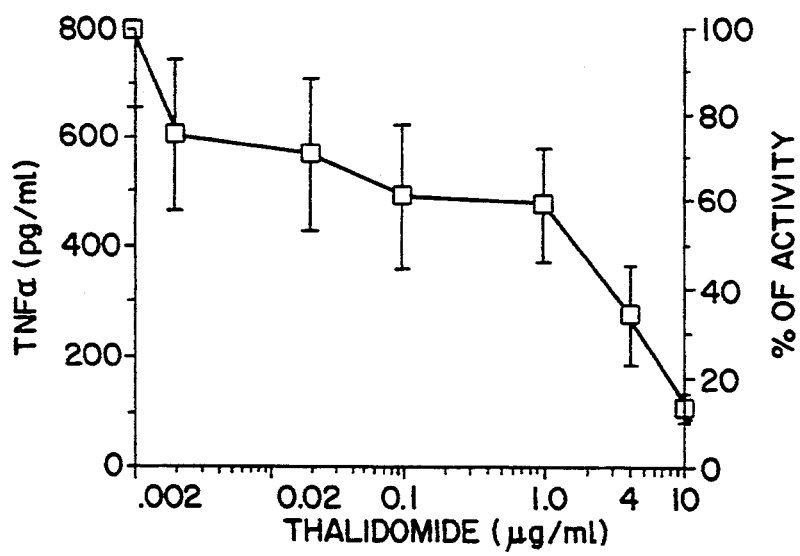
Figure 1B:
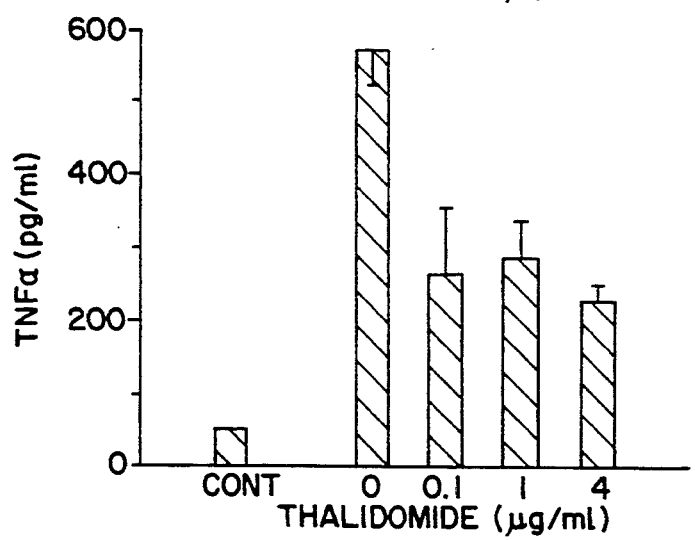
Figure 1C:
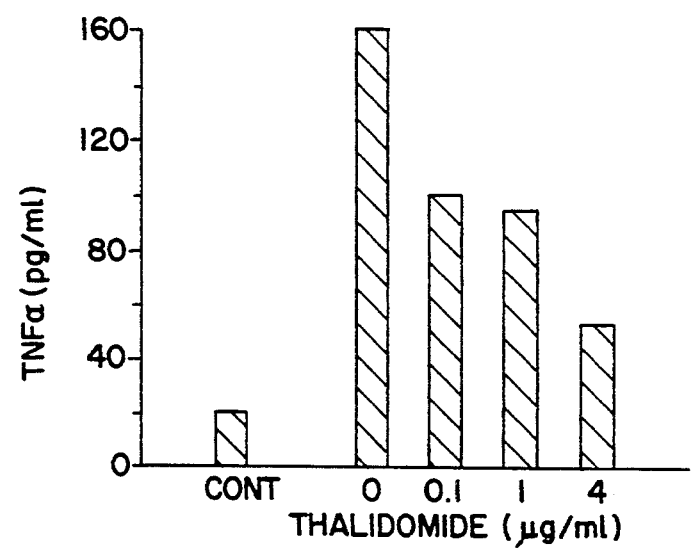
Figure 2:
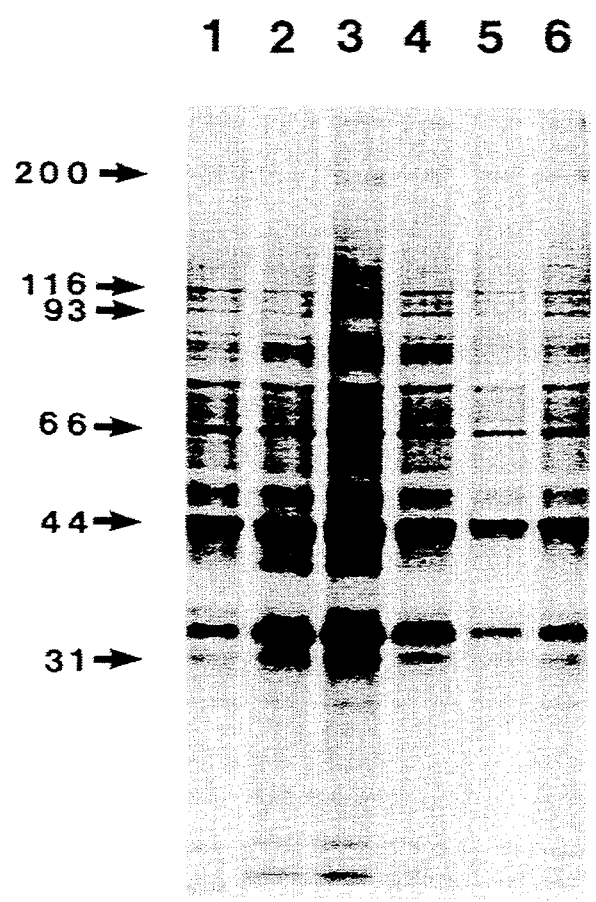
Figure 3A:
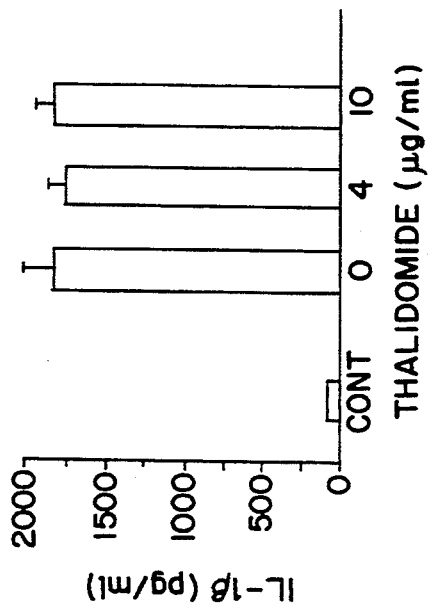
Figure 3B:
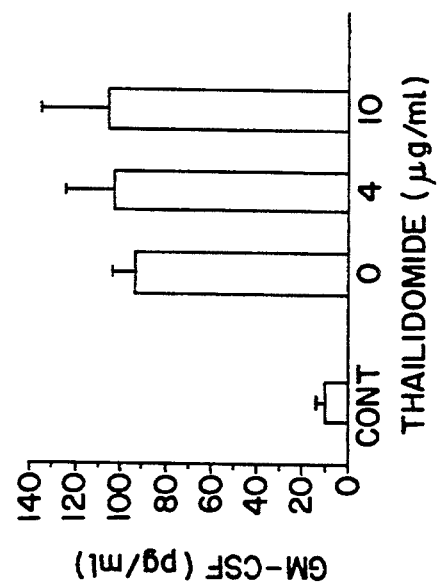
Figure 3C:
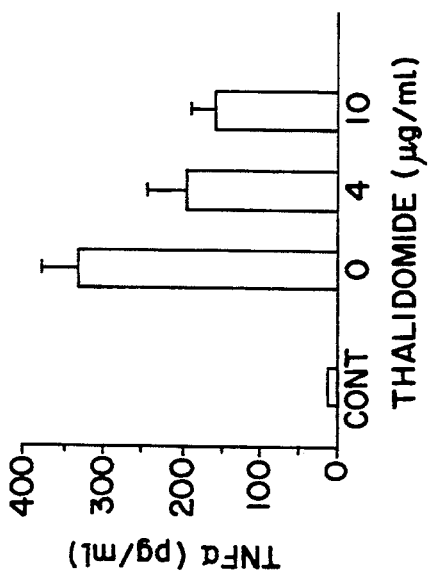
Figure 3D:
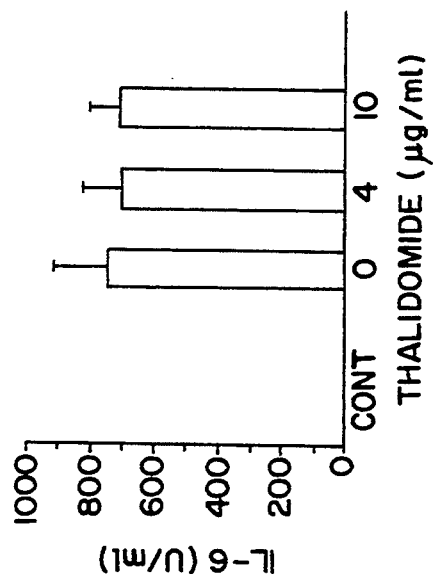
Figure 4:
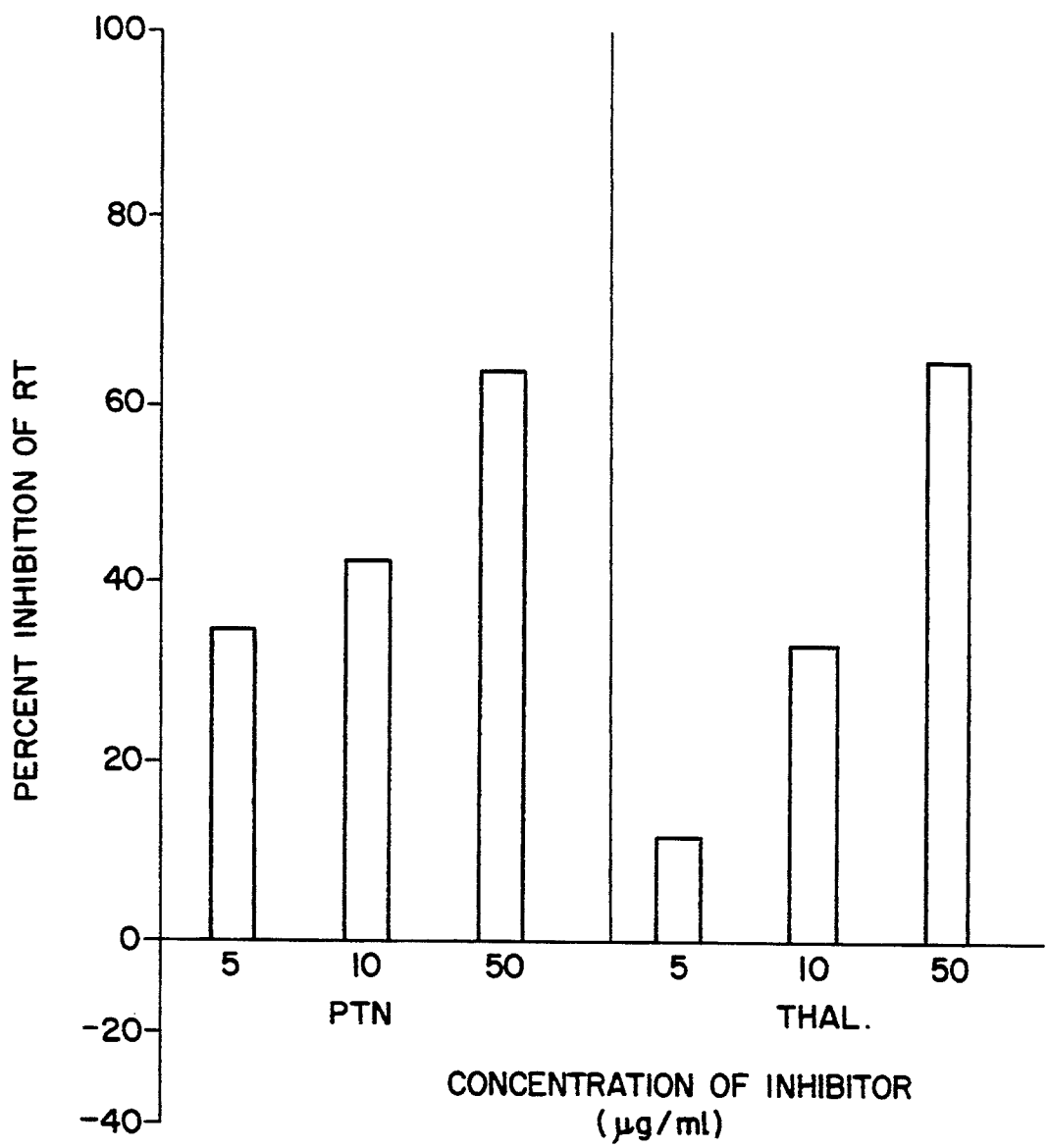
Figure 5:
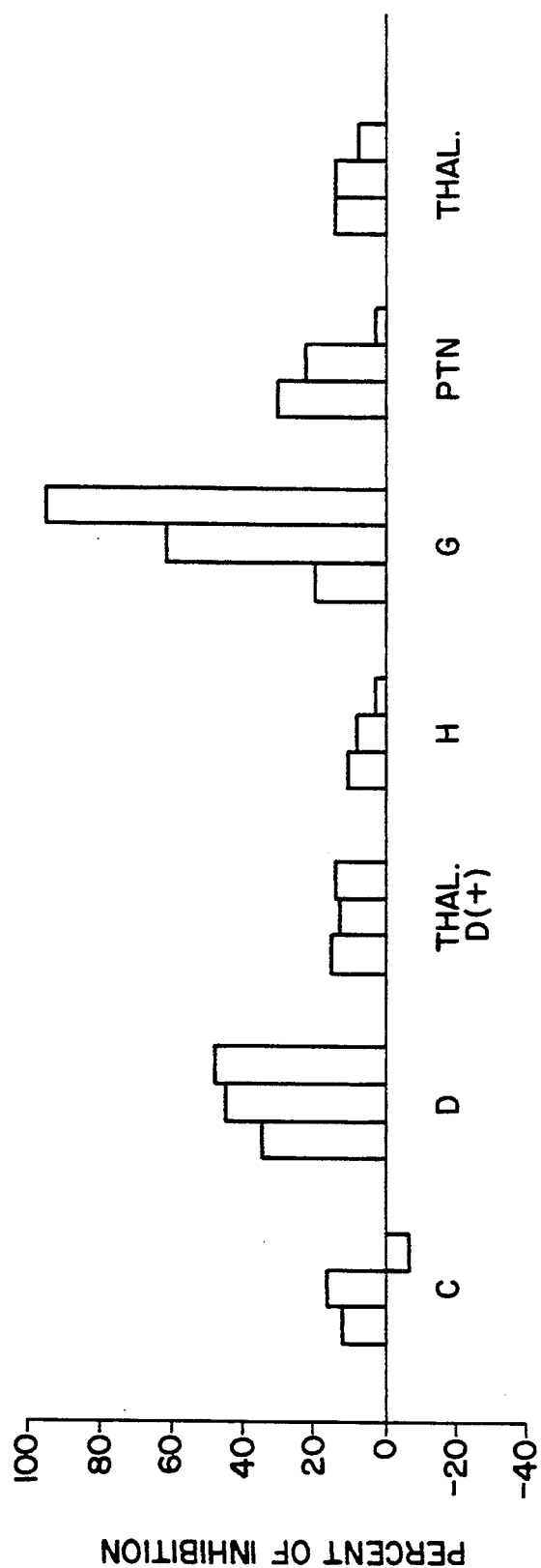
FIG. 5 shows the results of a similar test with a U1 cell line stimulated with PMA comparing thalidomide and PTN with other compounds of the invention including the D isomer of thalidomide. The other compounds of the invention are identified in this and the following figures by the letters used under their formulas hereinabove.
Figure 6:
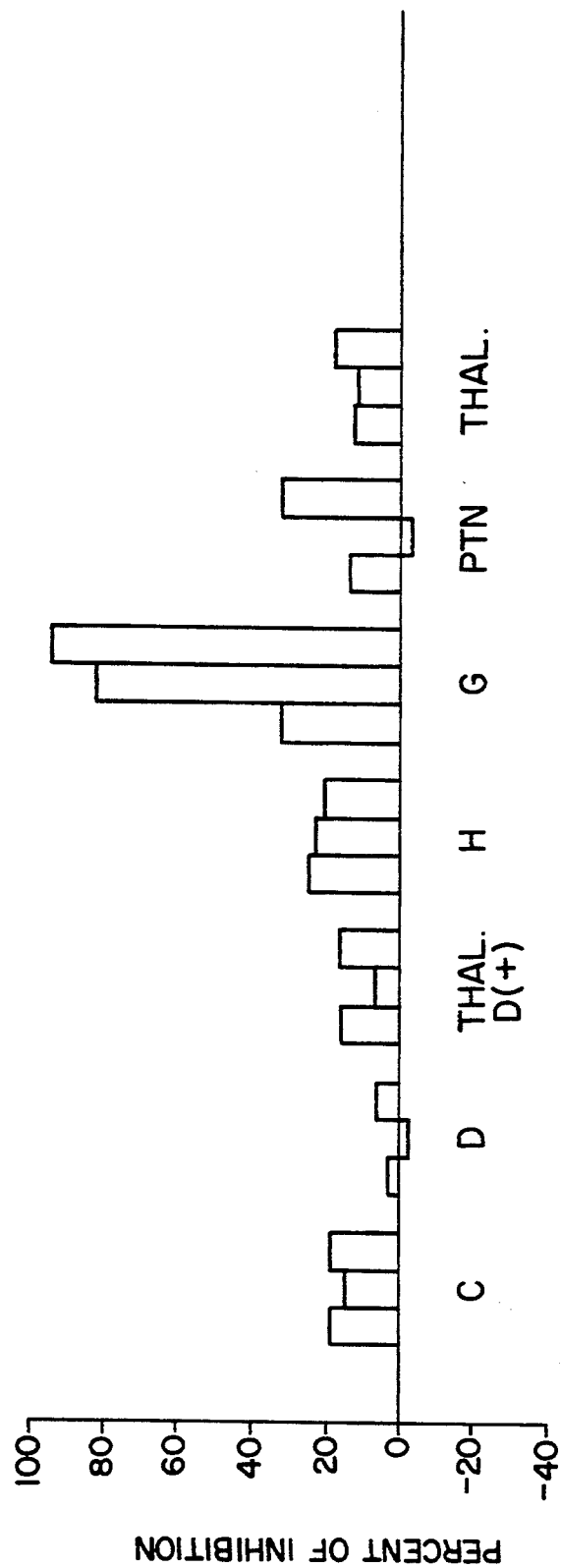
FIG. 6 shows a similar study in which the same compounds were tested with ACH-2 stimulated with TNF-$\alpha$.
Figure 7:
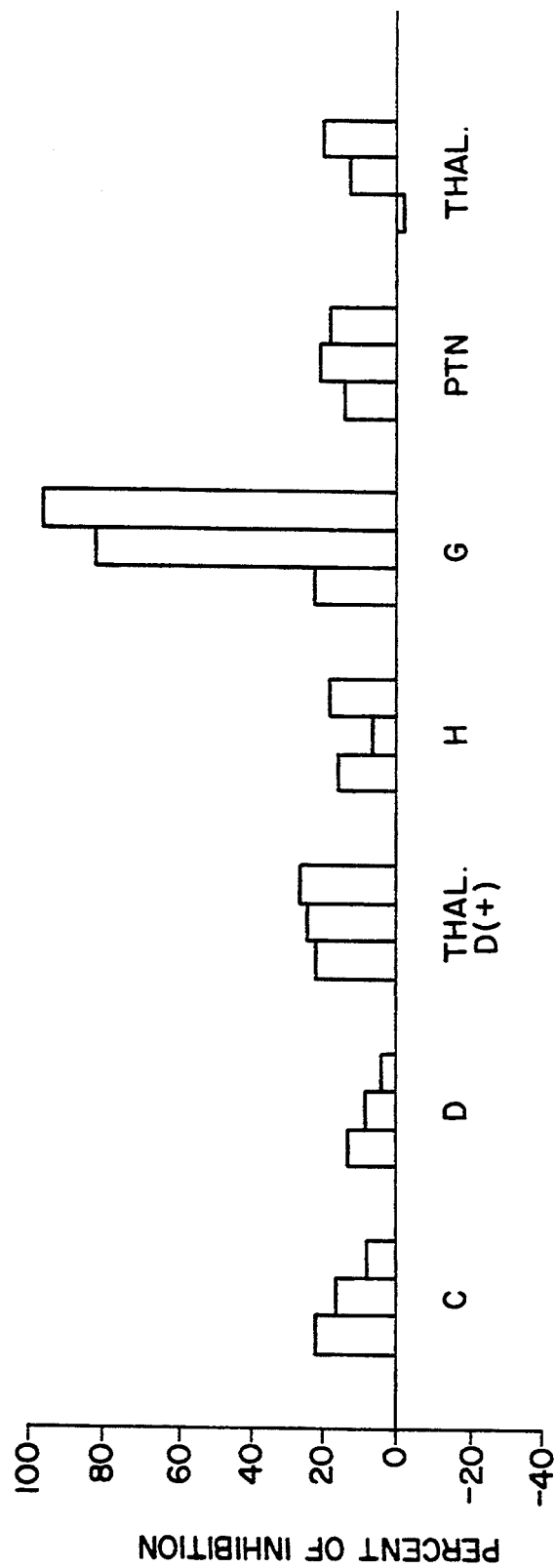

FIG. 7 records the results of a test using the ACH-2 cell line stimulated with PMA.

The compounds of the invention or their pharmaceutically acceptable salts may be administered perorally in a pharmaceutical carrier in standard form such as tablets, pills, lozenges, dragees and similar shaped and/or compressed preparations. It is also possible to produce emulsions or suspensions of the compounds in water or aqueous media such as unsweetened fruit juices and by means of suitable emulsifying or dispersing agents.

They may also be employed in the form of powders filled into gelatin capsules or the like.

Such powders and mixtures for use in the preparation of tablets and other shaped and/or compressed preparations may be diluted by mixing and milling with a solid pulverulent extending agent to the desired degree or firmness or by impregnating the already milled, finely powdered, solid carrier with a suspension of the compounds in water or with a solution thereof in an organic solvent and then removing the water or solvent.

When preparing tablets, pills, dragees, and the like shaped and/or compressed preparations, the commonly used diluting, binding, and disintegrating agents, lubricants, and other tableting adjuvants are employed, provided they are compatible with agent to be administered. Such diluting agents and other excipients are, for instance, sugar, lactose, levulose, starch, bolus alba; as disintegrating and binding agents, gelatin, gum arabic, yeast extract, agar, tragacanth, methyl cellulose, pectin: and as lubricants stearic acid, talc, magnesium stearate, and others.

They may be administered in the form of suppositories, typically utilizing such commonly used suppository vehicles, as cocoa butter.

The compounds may also be administered parenterally employing aqueous solutions or suspensions of watersoluble compounds or suspensions. The compositions may be made isotonic e.g. with salt or other solute and may contain a buffer, for example a phosphate buffer.

As indicated above, the compound employed in the invention may be the only active ingredient administered or it may be coadministered with another therapeutic agent in an amount which is effective to treat the condition associated with the debilitating effect. For example, if the cause of the condition is a toxin released by an infectious bacteria, an antibiotic such as tetracycline, penicillin, streptomycin and the like may be coadministered. If there is hypotension associated with lack of vascular tone, a vasopressive agent such as epinephrine or dopamine may be coadministered. If the patient is under treatment with a chemotherapeutic agent such as adriamycin, the compound of the invention and the chemotherapeutic agent may be coadministered.

The term "coadministered" does not mean that the compound of the invention and the additional therapeutic agent are administered in the same dosage unit, although they may be so administered. It means that they are administered within the same time span.

An "effective amount" of the compound or additional therapeutic agent will vary with the condition being treated, the age, weight and general physical condition of the patient under treatment and other factors readily evaluated by the physician in attendance.

What is claimed is:

1. The method of treating the toxic symptoms of high concentrations of $TNF_\alpha$ manifested in septic shock, cachexia, and HIV infection by inhibiting the production of $TNF_\alpha$ which comprises administering to a human susceptible to or exhibiting such symptoms an effective amount of a compound of the formula:

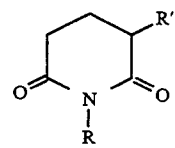

in which R is hydrogen, alkyl of 1 to 6 carbon atoms, phenyl, or benzyl, and

R' is

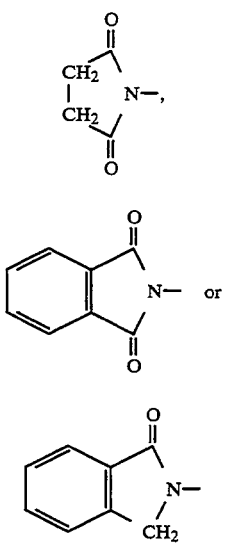

2. The method of claim 1 wherein R' is

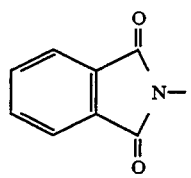

3. The method of claim 2 wherein said compound is 3-phthalimido-2,6-dioxopiperidine.

4. The method of claim 2 wherein said effective amount is sufficient to produce a blood level of said compound of at least 0.1 μg/mL.

5. The method of treating the debilitating effects of septic shock caused by high concentrations of $TNF_\alpha$ by inhibiting production of $TNF_\alpha$ which comprises administering to a human susceptible to or exhibiting such effects an effective amount of a compound of the formula:

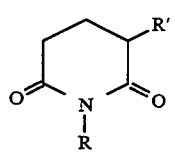

in which R is hydrogen, alkyl of 1 to 6 carbon atoms, phenyl, or benzyl, and

R' is

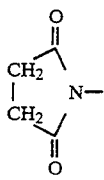

or

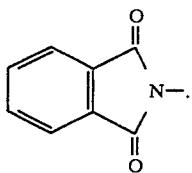

6. The method of claim 5 wherein R' is

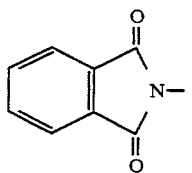

7. The method of claim 6 wherein said compound is 3-phthalimido-2,6-dioxopiperidine.

8. The method of claim 6 wherein said effective amount is sufficient to produce a blood level of said compound of at least 0.1 μg/mL.

9. The method of treating the debilitating effects of cachexia caused by high concentrations of $TNF_\alpha$ by inhibiting production of $TNF_\alpha$ which comprises administering to a human susceptible to or exhibiting such effects an amount of a compound of the formula:

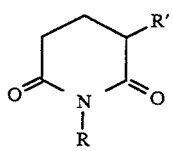

in which R is hydrogen, alkyl of 1 to 6 carbon atoms, phenyl, or benzyl, and
R' is

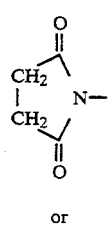

or

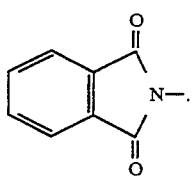

10. The method of claim 9 wherein R' is

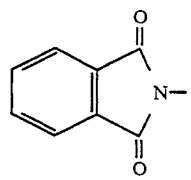

11. The method of claim 10 wherein said compound is 3-phthalimido-2,6-dioxopiperidine.

12. The method of claim 10 wherein said effective amount is sufficient to produce a blood level of said compound of at least 0.1 μg/mL.

13. The method of treating the debilitating effects of an HIV infection caused by high concentrations of $TNF_\alpha$ by inhibiting production of $TNF_\alpha$ which comprises administering to a human susceptible to or exhibiting such effects an amount of a compound of the formula:

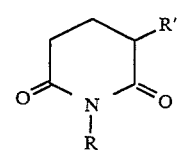

in which R is hydrogen, alkyl of 1 to 6 carbon atoms, phenyl, or benzyl, and
R' is

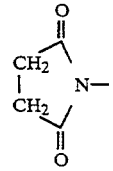

or

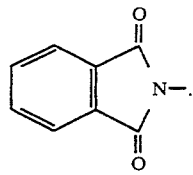

14. The method of claim 13 wherein R' is

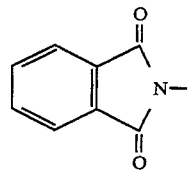

15. The method of claim 14 wherein said compound is 3-phthalimido-2,6-dioxopiperidine.

16. The method of claim 14 wherein said effective amount is sufficient to produce a blood level of said compound of at least 0.1 μg/mL.

17. The method of treating the toxic symptoms of high concentrations of $TNF_\alpha$ manifested in septic shock, cachexia, and HIV infection by inhibiting the production of $TNF_\alpha$ which comprises administering to a human susceptible to or exhibiting such symptoms an effective amount of a compound of the formula:
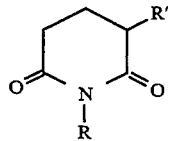
in which R is allyl or morpholinomethyl, and
R' is
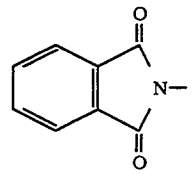
or
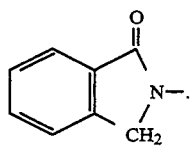
18. The method of claim 17 wherein said effective amount is sufficient to produce a blood level of at least 0.1 µg/mL.
* * * * *